United States Patent [19]

White et al.

[11] Patent Number: 5,212,988

[45] Date of Patent: May 25, 1993

[54] PLATE-MODE ULTRASONIC STRUCTURE INCLUDING A GEL

[75] Inventors: Richard M. White; Stuart W. Wenzel, both of Berkeley; Benedict J. Costello, Oakland, all of Calif.

[73] Assignee: The Regents of the University of California, Berkeley, Calif.

[21] Appl. No.: 775,631

[22] Filed: Oct. 10, 1991

Related U.S. Application Data

[63] Continuation-in-part of Ser. No. 467,412, Jan. 18, 1990, Pat. No. 5,129,262, which is a continuation of Ser. No. 162,193, Feb. 29, 1988, abandoned.

[51] Int. Cl.⁵ ............................................. G01N 29/00
[52] U.S. Cl. ........................................ 73/599; 73/602
[58] Field of Search ................. 73/599, 602, 590, 597, 73/589, 601, 632; 310/313 R, 313 A, 313 B; 333/147, 149

[56] References Cited

U.S. PATENT DOCUMENTS

| | | | |
|---|---|---|---|
| 3,786,373 | 1/1974 | Schulz et al. | 333/30 R |
| 3,878,477 | 4/1975 | Dias et al. | 331/40 |
| 3,965,444 | 6/1976 | Willingham et al. | 333/30 R |
| 4,361,026 | 11/1982 | Muller et al. | 73/23 |
| 4,404,852 | 9/1983 | Goto | 73/599 |
| 4,456,850 | 6/1984 | Inoue et al. | 310/324 |
| 4,463,336 | 7/1984 | Black et al. | 338/4 |
| 4,480,209 | 10/1984 | Okamoto et al. | 310/313 B |
| 4,598,224 | 7/1986 | Ballato | 310/313 R |
| 4,623,813 | 11/1986 | Naito et al. | 73/703 |
| 4,670,092 | 6/1987 | Motamebi | 73/720 |
| 4,672,354 | 6/1987 | Kurtz et al. | 73/DIG. 4 |
| 4,805,456 | 2/1989 | Howe et al. | 73/DIG. 1 |
| 5,129,262 | 7/1992 | White et al. | 73/599 |

FOREIGN PATENT DOCUMENTS

| | | | |
|---|---|---|---|
| 1191817 | 11/1985 | U.S.S.R. | 73/23 |
| 1330142 | 9/1973 | United Kingdom | 333/150 |

OTHER PUBLICATIONS de Klerk, J., "Ultrasonic Transducers," Ultrasonics, vol. 9, No. 1, Jan. 1971, pp. 35–48 (310/333).
Toda, K., et al., "A Lamb wave voltage sensor," J. Acoust. Soc. Am., vol. 74(3), pp. 677–679, Sep. 1983.
Uozumi, et al., "Generation and detection of ultrasonic Lamb waves in a thin deposited film by using interdigital transducers," Applied Physics Letters, vol. 43(1), pp. 917–919, Nov. 1983.
Viktorov, I. A., "Raleigh and Lamb Waves," Plenum Press, N.Y., 1967, (tr. from Russian) Ch. 1, pp. 1–7; Ch. 11, pp. 67–77.
Peterson, K. E., et al., "Young's Modulus Measurement of Thin Films Using Micromechanics," J. Applied Physics, vol. 50(11), pp. 6761–6766, Nov. 1979.

*Primary Examiner*—Louis Arana
*Attorney, Agent, or Firm*—Heller, Ehrman, White & McAuliffe

[57] ABSTRACT

An ultrasonic structure which has a thin planar sheet of material forming a Lamb wave propagation medium The propagation medium is coated with a gel. The structure may also include a Lamb wave generator for generating Lamb waves in the propagation medium and an output device for producing an electrical signal representative of the propagation characteristics of the Lamb waves propagating along the propagation medium. A measuring device can be included to measure selected characteristics of the output electrical signal. The propagation medium has some physical characteristics that are determined by the value of a measurand acting on the medium and the determined physical characteristics determine the propagation characteristics of the Lamb waves which are propagated along the medium. When the sensor is acted on by a measurand to determine the physical characteristics of the propagation medium, the characteristics of the electrical signal are also determined. The measuring device measures the electrical signal and provides an indication of the measurand value.

42 Claims, 8 Drawing Sheets

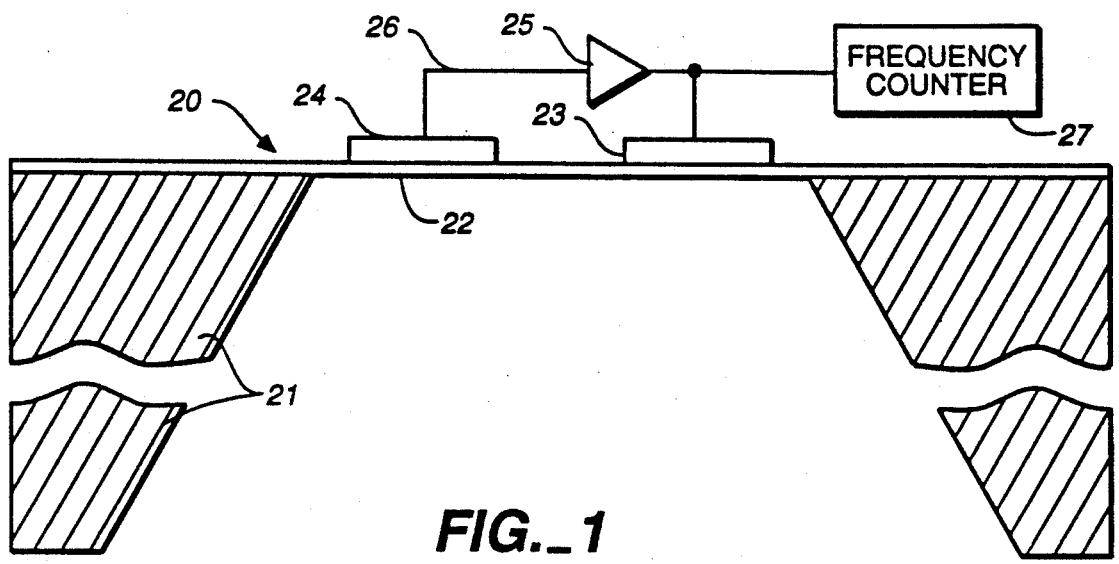
FIG._1
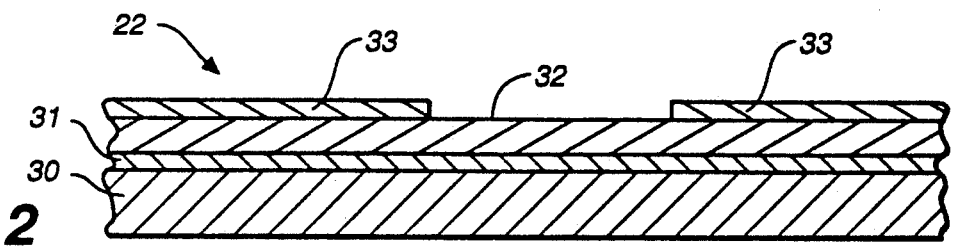
FIG._2
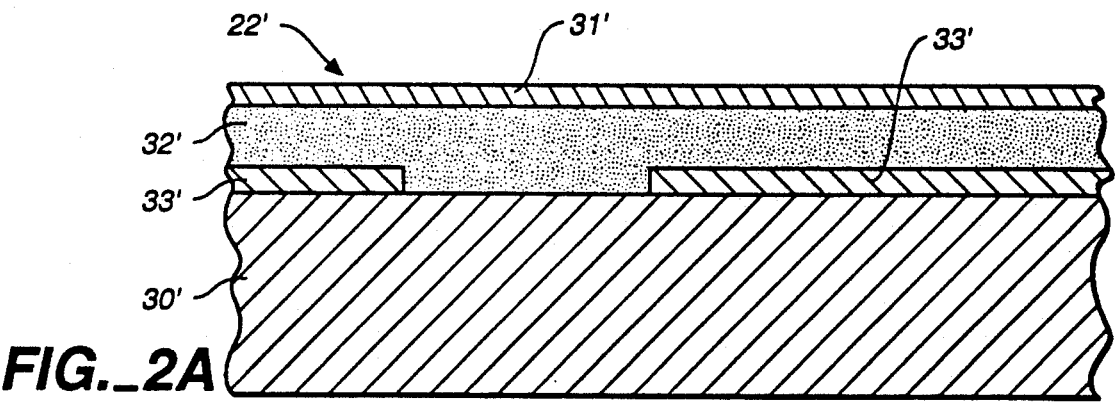
FIG._2A
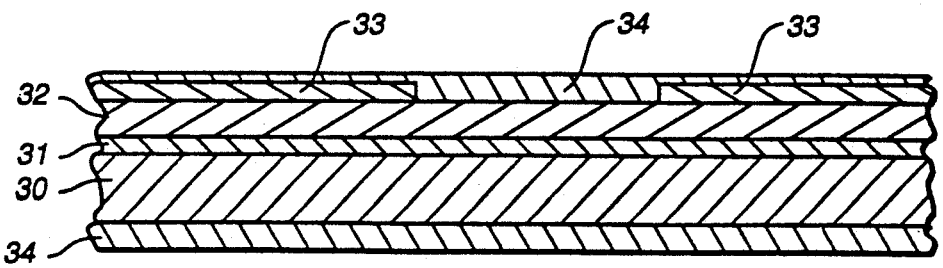
FIG._3

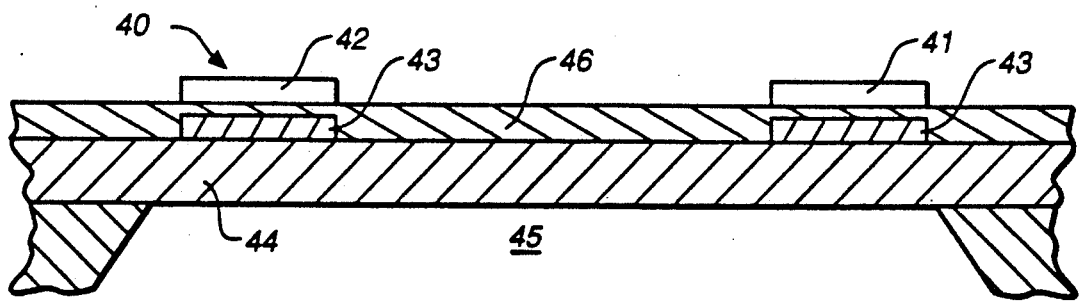
FIG._4
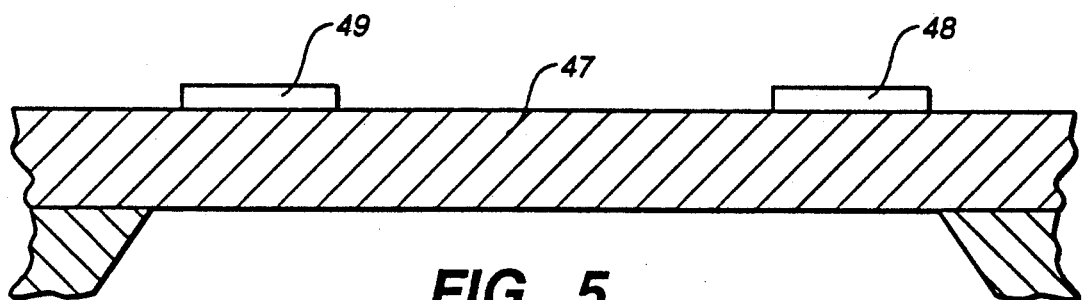
FIG._5
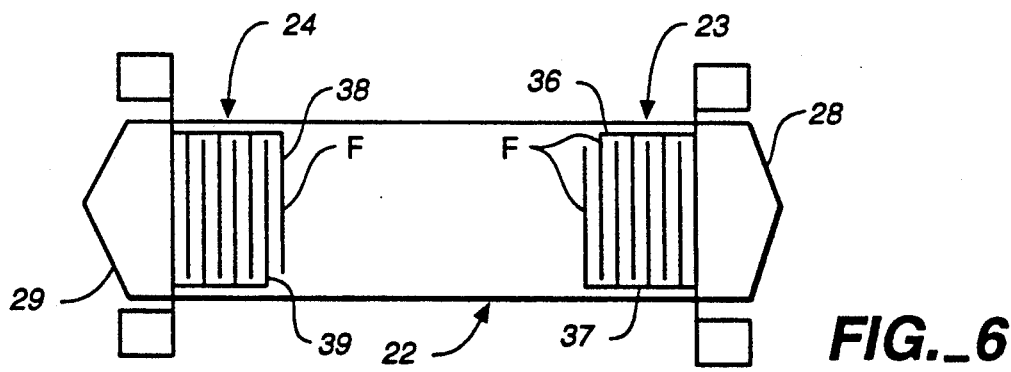
FIG._6
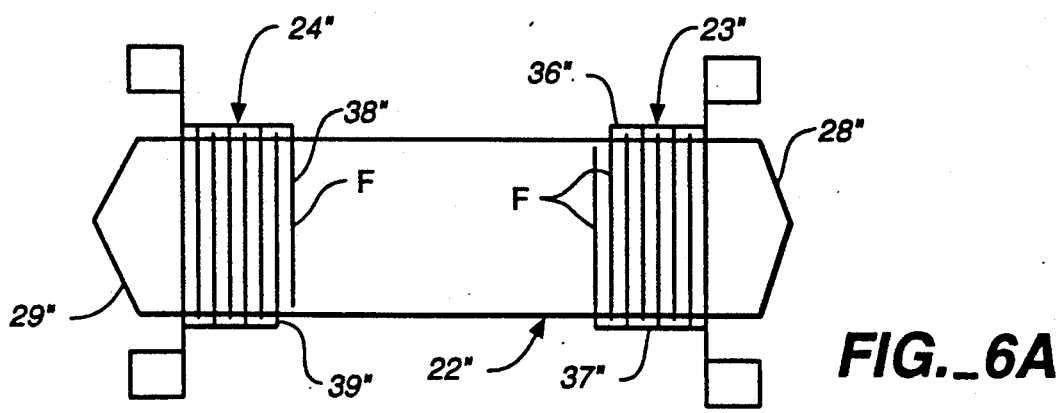
FIG._6A

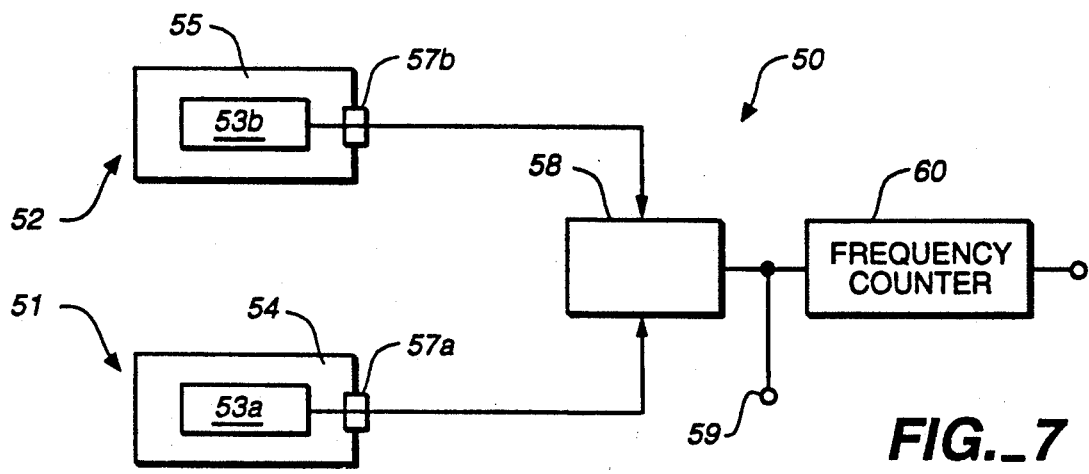
FIG._7
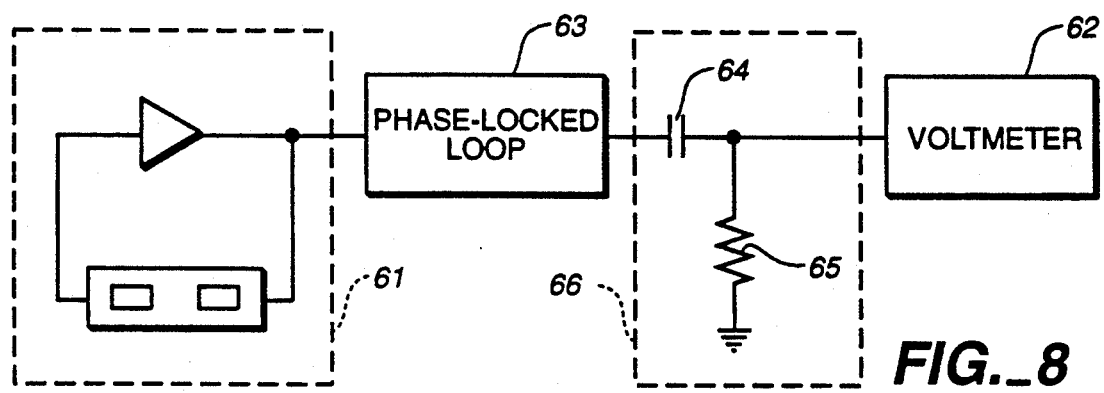
FIG._8
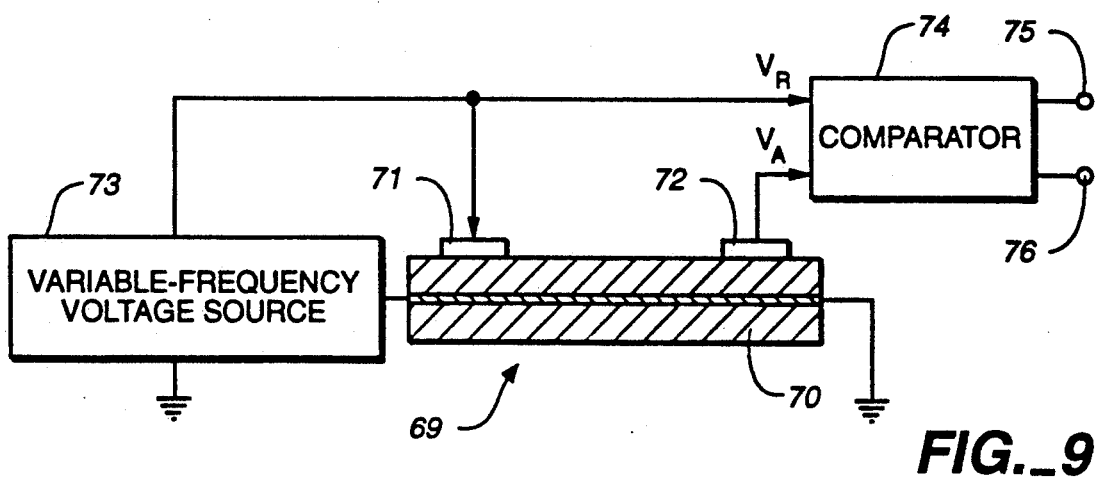
FIG._9

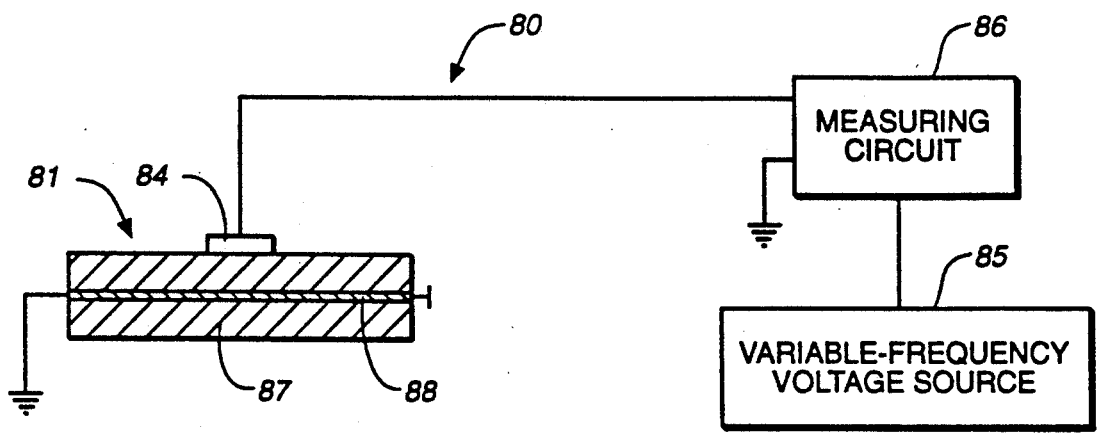
FIG._10
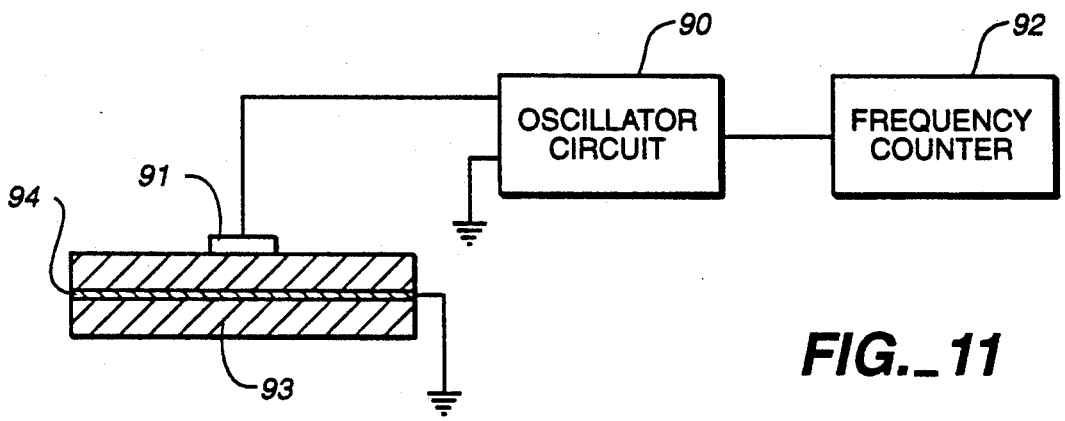
FIG._11
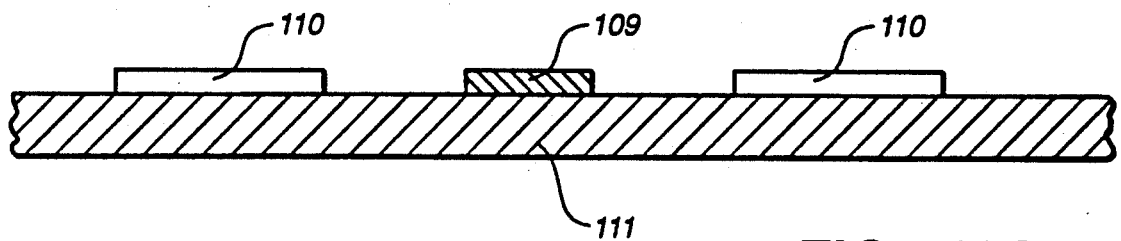
FIG._11A

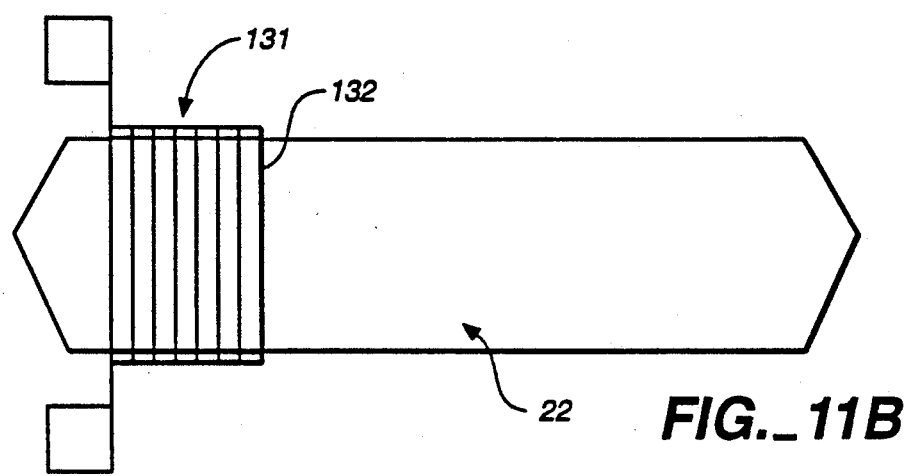
FIG._11B
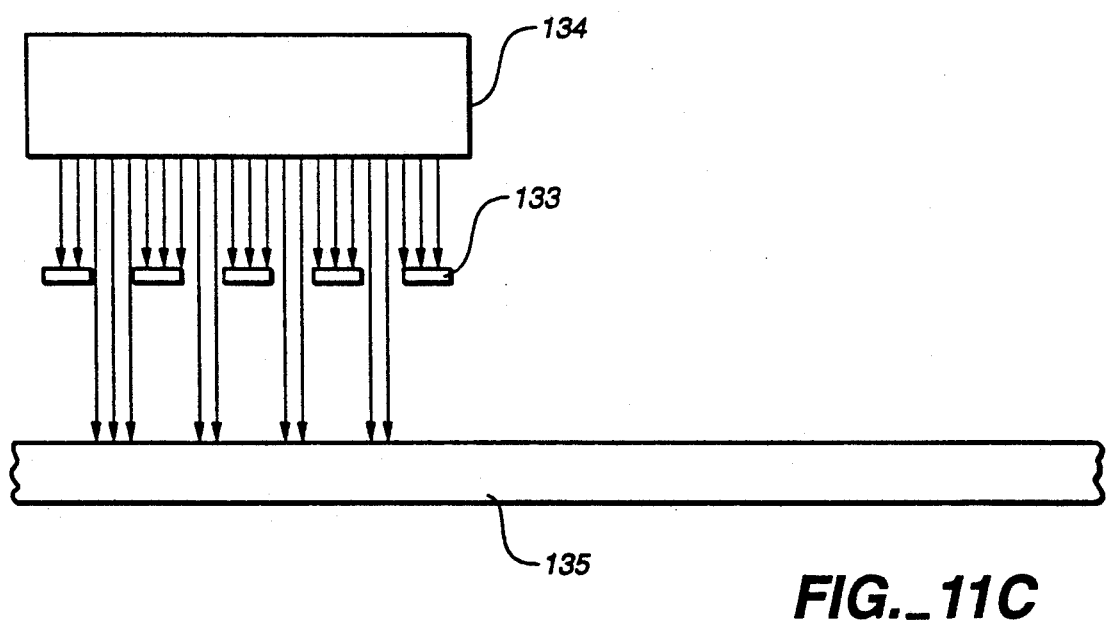
FIG._11C

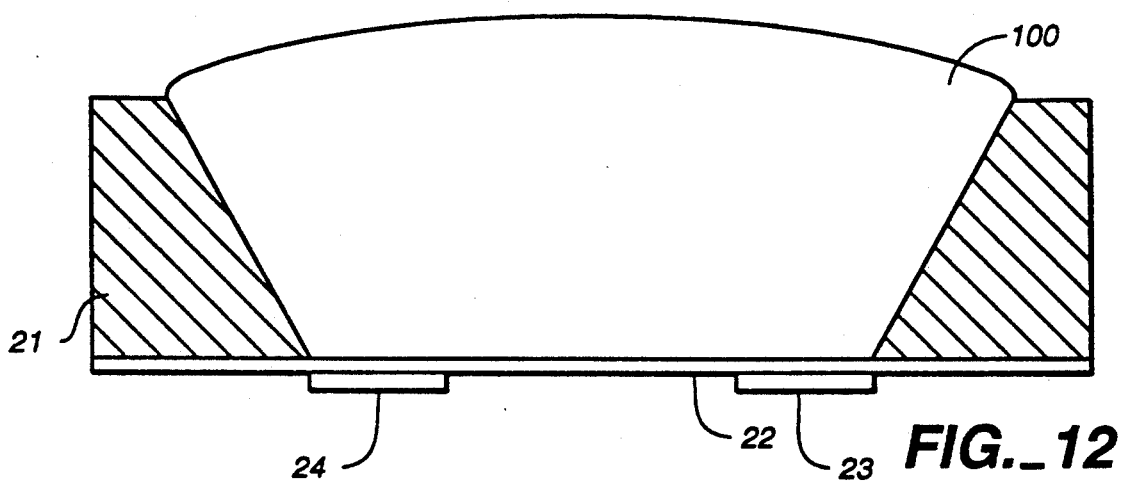
FIG._12
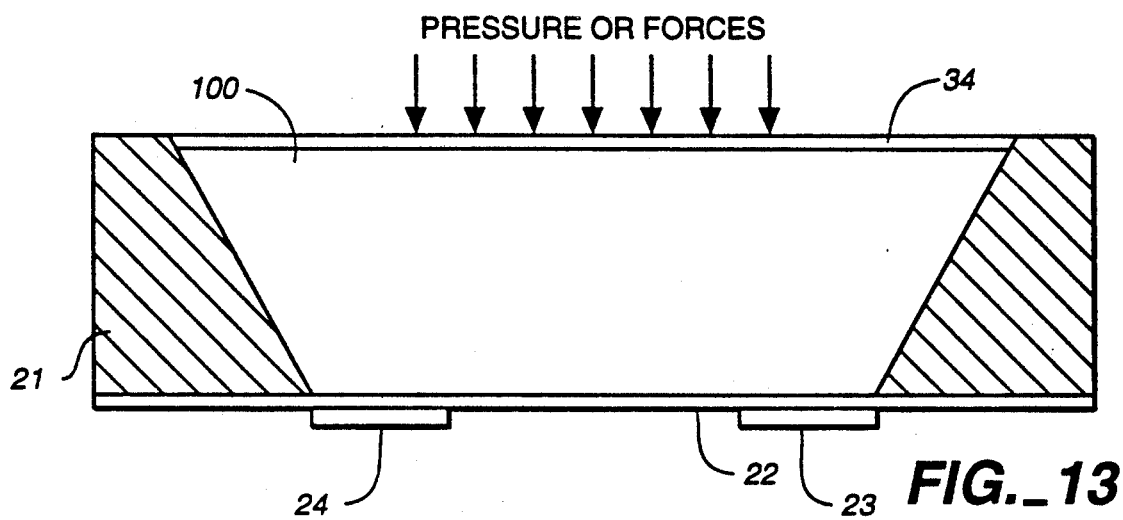
FIG._13
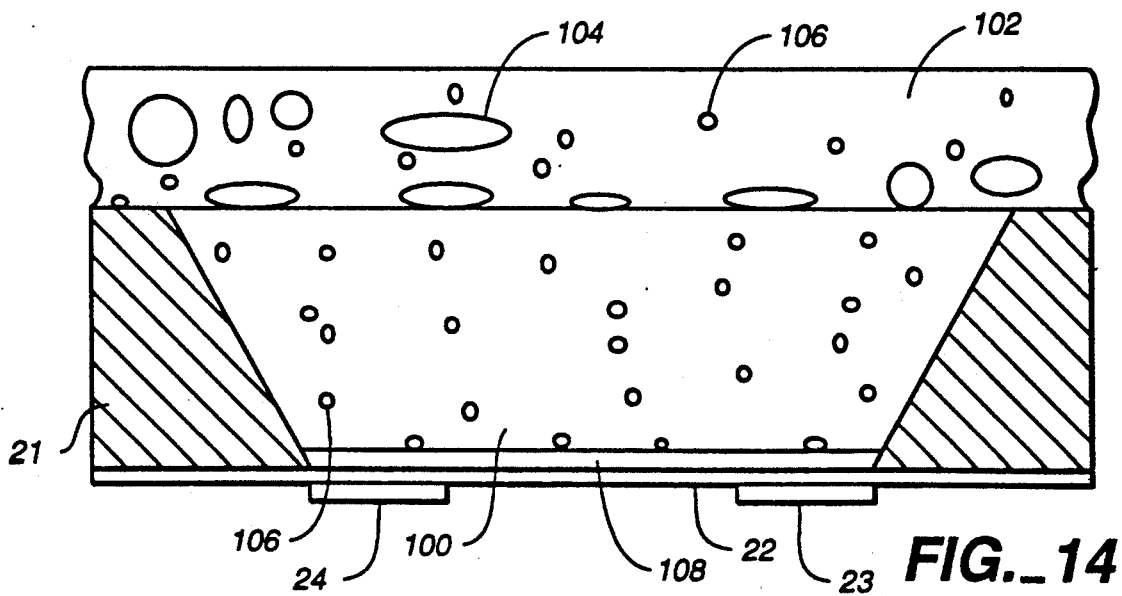
FIG._14

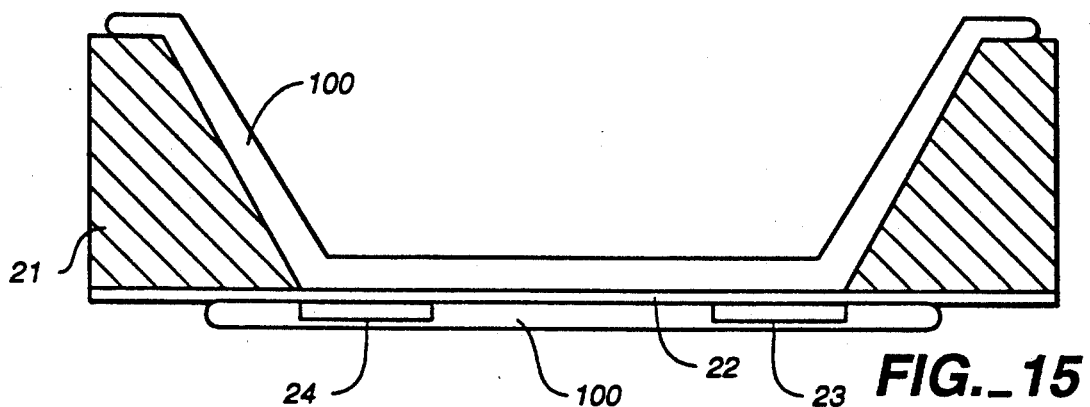
FIG._15
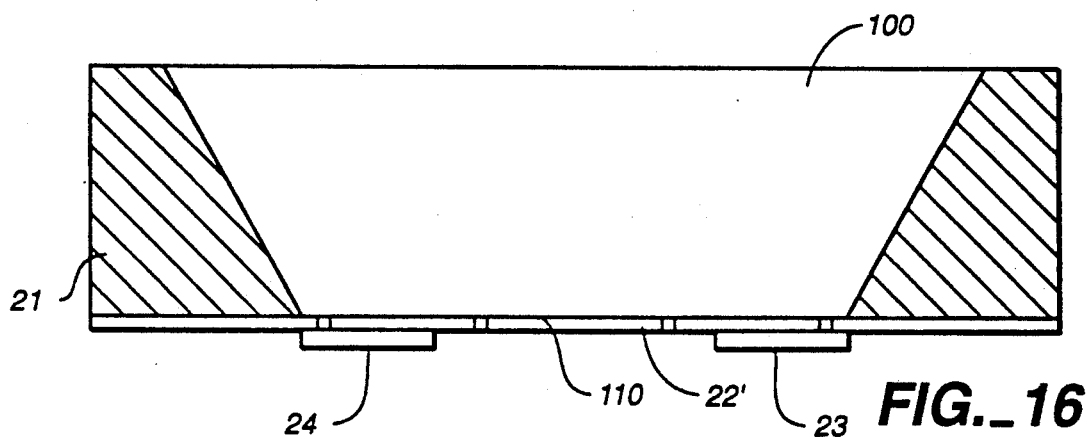
FIG._16
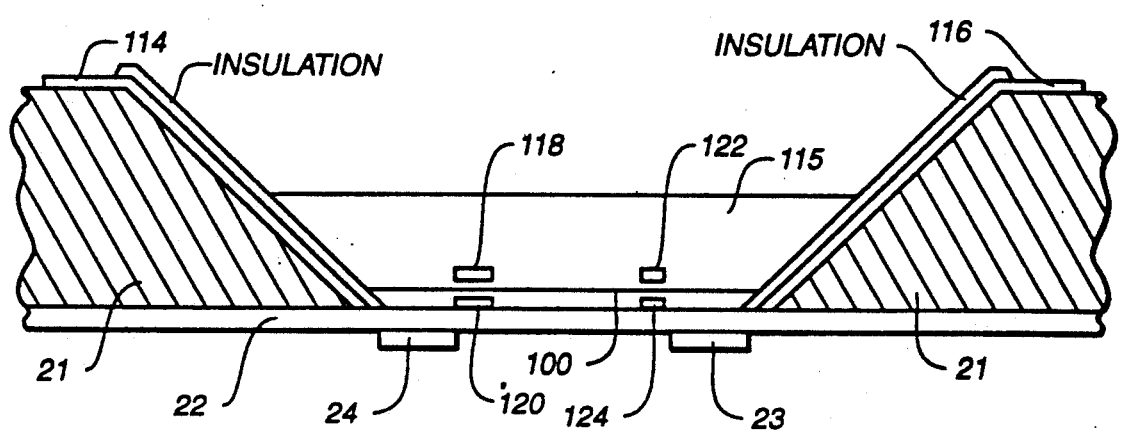
FIG._17

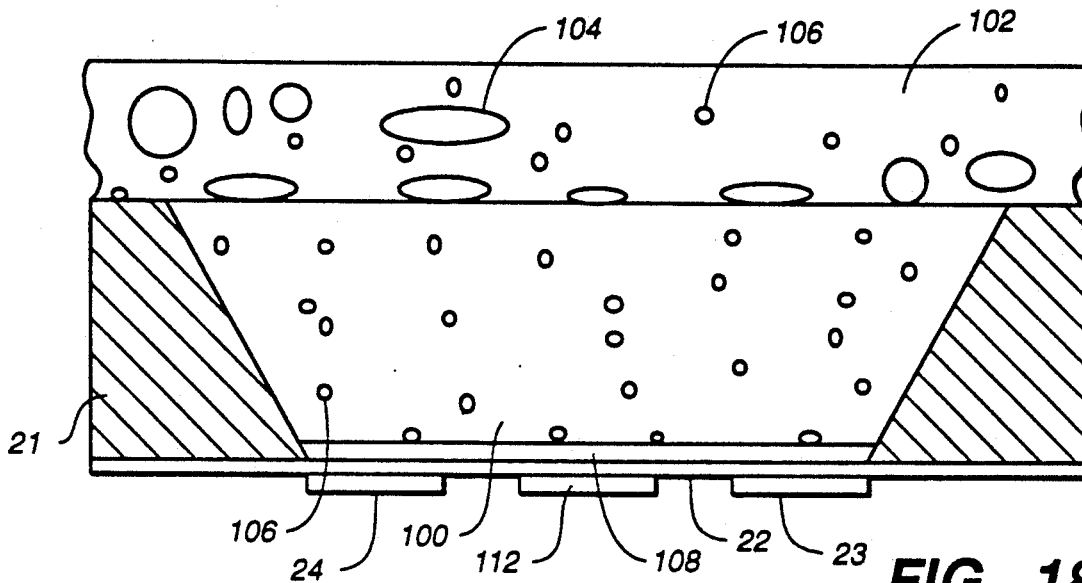
FIG._18
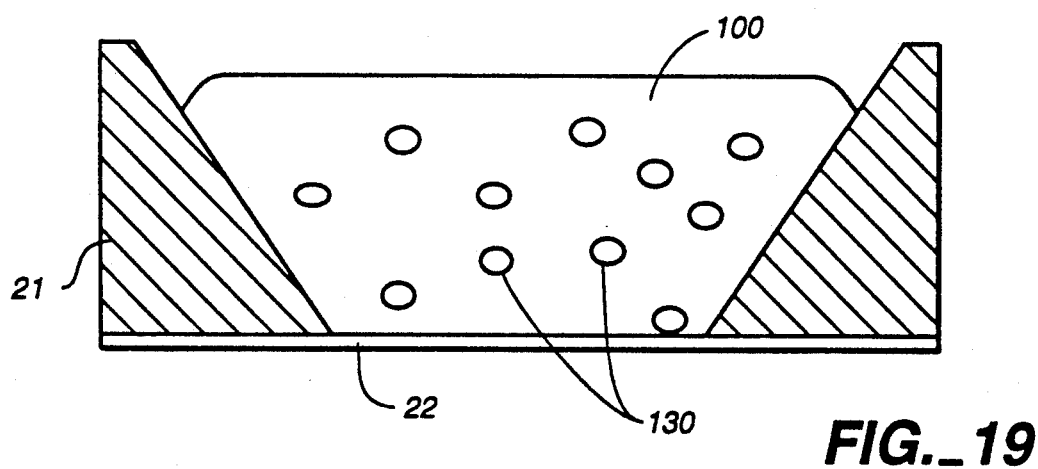
FIG._19

PLATE-MODE ULTRASONIC STRUCTURE INCLUDING A GEL

This application is a continuation-in-part of application Ser. No. 07/467,412, filed Jan. 18, 1990 now U.S. Pat. No. 5,129,262, which is a continuation of application Ser. No. 07/162,193, filed Feb. 29, 1988 now abandoned. The entire disclosures of both of these applications are hereby incorporated by reference.

This invention relates to ultrasonic structures, and to ultrasonic sensing devices which utilize Lamb waves to sense changes in a measurand or to determine the value of a measurand.

The invention also relates to an apparatus for generating, receiving, and processing Lamb waves and to an apparatus utilizing Lamb waves for sensing and quantifying phenomena hitherto either not sensed or not quantified with sufficient accuracy.

BACKGROUND OF THE INVENTION

The phenomenon responsible for the operation of ultrasonic oscillator sensors is elastic wave propagation along a medium whose characteristics can be altered by a measurand. Where the characteristics of the waves propagating along the medium are dependent upon the characteristics of the propagation medium, the wave characteristics can be monitored or measured to provide an indication of the measurand value.

Many sensing applications have been found for Rayleigh or surface acoustic waves (SAWs). However, SAWs can only propagate through a semi-infinite medium, that is, a medium having a thickness which is many times their wavelength. The propagation medium used by SAW sensors is commonly a piezoelectric substrate or a piezoelectric-coated substrate, the piezoelectric material cooperating with transducing electrode structures to generate and receive the SAWs.

SAW devices are shown, for example, in U.S. Pat. No. 3,878,474 to Dias and Karrer, in which a SAW oscillator is employed as a force-sensing device, and in U.S. Pat. No. 3,786,373 to Schulz and Holland, which discloses a temperature-compensated SAW resonator device which is not specifically designed for use as a sensing element. The latter patent includes a double substrate arrangement in which interdigital electrode arrays are disposed upon a substrate which may be deposited upon the surface of a non-piezoelectric layer which, in turn, is placed upon the surface of a piezoelectric substrate giving a propagation medium that is thick relative to the wavelength of the SAWs.

U.S. Pat. No. 3,965,444 to Willingham et al. shows another temperature-compensated SAW device, having a $SiO_2$ film layer on a substrate of piezoelectric material; and U.S. Pat. No. 4,480,209 to Okamoto, et al. shows a SAW device with a silicon substrate that is thick compared to the wavelength of the SAWs, together with a zinc oxide piezoelectric layer deposited thereon.

U.S. Pat. No. 4,456,850 to Inoue et al. shows a high-frequency piezoelectric composite "thin-film" resonator in a fundamental thickness-extensional vibration mode. It is said to have good temperature stability and resonance response. Inoue uses "thin films" having particular resonant frequency characteristics, but only as part of a thick sandwiched structure having the piezoelectric materials to achieve the temperature stability.

A number of problems arise in SAW sensing devices due to SAW characteristics or to the characteristics of the medium required for SAW propagation. One such problem is that it is difficult to operate SAW sensors while they are immersed in most liquids, a problem rendering them inappropriate for many biological and chemical sensing applications. The reason is that when SAW devices are immersed, the SAW velocity is higher than the velocity of sound waves through the liquid; a large amount of the SAW energy is therefore radiated into the liquid, and the wave is attenuated as it travels along the propagation medium.

Another problem with SAW sensors is that the thickness of the SAW propagation medium makes such devices inappropriate for certain sensor applications. Furthermore, SAW sensor devices lack the degree of sensitivity required for many possible sensor applications.

A voltage sensor which utilizes a Lamb wave delay line oscillator has been proposed by K. Toda and K. Mizutoni in the *Journal of the Acoustical Society of America*, Vol. 74(3), pages 677-79, 1983. The delay line uses a piezoelectric ceramic plate with a third electrode that changes the acoustic path length of the piezoelectric plate in response to an applied voltage. Although the ceramic plate is capable of supporting Lamb waves, it is still a relatively thick medium, having a thickness of 180 micrometers. This ceramic plate thickness is required for mechanical stability. However, this propagation medium thickness decreases the sensitivity of the voltage sensor and increases the velocity of flexural Lamb waves which propagate therethrough. Also the thickness required of the Toda/Mizutomi propagation medium results in a device that is ill-suited for many potential sensing applications.

A metallic Lamb-wave structure has been proposed by Uozumi et al. for use in measuring the elastic properties of thin metallic films as described in *Applied Physics Letters*, Vol. 43(10), pages 917-19, 1983. The Uozumi et al. Lamb-wave structure teaches a Lamb wave propagation medium that includes a metal base material on which is formed a piezoelectric film. The metallic base layer is formed by plating copper, to a thickness of three microns, onto an evaporated copper film on a disposable substrate. The piezoelectric film is deposited on this base material and transducer electrodes are deposited on the piezoelectric film to form a delay line structure.

The structure shown by Uozumi et al. is difficult to fabricate and the resulting propagation medium is wrinkled out of its plane due to the compressive stresses developed on the metallic base layer during piezoelectric film deposition that deform the metallic layer substantially. This is in contrast to the Lamb-wave sensor of the present invention, which has a propagation medium that is planar in form, even on its small scale. Also, propagation media pursuant to the teachings of Uozumi et al. are inappropriate for many possible sensor applications due to the properties of the metallic base material.

It is therefore an object of the invention to provide an ultrasonic sensor which exhibits high sensitivity.

Another object is to provide an ultrasonic sensor having sensitivity at least an order of magnitude greater than the best SAW device currently available.

Another object is to provide an ultrasonic sensor having a small heat capacity so that it can respond rapidly to heating.

A further object of the invention is to provide an ultrasonic sensor device that can operate fully satisfactorily while immersed in fluids of most types.

These and other objects, advantages, and features of the invention will be apparent from the following summary of the invention and description of preferred embodiments, considered along with the accompanying drawings.

SUMMARY OF THE INVENTION

The invention marks a departure from the use of SAWs or Rayleigh waves in ultrasonic sensors and employs instead Lamb waves, which are also known as plate-mode waves. Lamb waves can propagate only through a material of finite thickness. In contrast to SAWs, which require a propagation medium having a thickness on the order of tens to hundreds of times the wavelength of the SAW propagating therethrough, Lamb waves require a propagation medium which is at most only several wavelengths thick.

The invention also marks a departure from the previously proposed Lamb wave voltage sensor, which uses a relatively thick but finite medium and relies only on a change in acoustic path length to detect a measurand. In contrast, the sensor according to the invention uses a very thin propagation medium which can be affected by a measurand in several different ways to produce a sensor output. Also, the sensor pursuant to this invention is capable of taking advantage of special Lamb wave characteristics that arise in plates whose thickness is comparable with or small as compared to the wavelength of the wave.

The invention is directed to an ultrasonic structure including a thin propagation medium capable of supporting Lamb waves. The propagation medium may include on a surface thereof a layer of a low shear modulus material.

The invention may further include generating means for generating Lamb waves along the propagation medium, conversion means for converting the Lamb waves into electrical signals representative of the waves, and measuring means for measuring certain characteristics of the electrical signals which represent the Lamb waves propagating along the medium.

The wave-generating means cause Lamb waves to propagate along the propagation medium, the medium also having material characteristics which can be altered by a measurand. Changes in the propagation medium characteristics, in turn, cause changes in the wave characteristics of the Lamb waves propagating along the medium. The Lamb wave characteristics are measured or monitored by the measuring means to detect changes in, or to determine the value of, a measurand.

The propagation medium comprises a very thin planar sheet of material which is capable of supporting Lamb wave propagation, and is preferably much thinner than the wavelength of the particular Lamb waves. For example, where the wavelength of the Lamb waves is on the order of 100 microns, the propagation medium is preferably approximately only a few microns thick or no greater than twenty microns. The propagation medium of a sensor according to this invention may have a thickness up to about two times the wavelength of the waves to be propagated through the medium. However, lesser thicknesses are readily obtainable and may be required to provide desired sensor characteristics for a particular application or to take advantage of special Lamb wave characteristics that arise in very thin plates.

The propagation medium may also be referred to as an acoustically-thin plate or a membrane. Strictly speaking, it is neither a "plate" nor a "membrane" as those terms are usually defined in the mechanical engineering literature. Unlike such plates, the present plate is so thin that its elastic response to deformation can be influenced by in-plane tension that develops during the initial fabrication process. Also, since flexural Lamb waves can propagate on these structures, they are unlike membranes, which are formally regarded as being infinitely flexible. However, in spite of these formal differences, the terms "propagation medium", "plate", and "membrane" will be defined, for the purposes of this specification, and unless otherwise specified, as any structure capable of supporting Lamb wave propagation. Also, the term "Lamb waves" will be defined, for the purposes of this specification, as any elastic wave that propagates in a finite medium regardless of in-plane tension or lack of such tension in the propagation medium.

Since the propagation medium thicknesses are generally in the order of several microns, semiconductor microfabrication materials and techniques are preferably employed in the construction of the membrane. For example, in a preferred form, the membrane is formed on a silicon wafer and comprises a layer of silicon nitride, a layer of aluminum or other conducting material, and a layer of piezoelectric zinc oxide. A portion of the silicon beneath the silicon nitride layer is etched away to leave a thin membrane, supported along at least a portion of its periphery by the remaining silicon wafer.

The sensor uses a transducer structure coupled to the propagation medium to generate both symmetrical and antisymmetrical mode Lamb waves in the medium. In one form, the transducer electrodes differentially deform a piezoelectric material that forms a layer of the propagation medium to produce a mechanical wave motion in the medium. In another form, the transducer electrodes can produce a sufficient electric field intensity to produce Lamb waves in the propagation medium without the need for a piezoelectric material. The latter form of Lamb-wave generation may be referred to as "electrostriction." In a third form, periodic heating is applied to the plate by optical or electrical means to produce Lamb waves thermoelastically.

In one form, the Lamb-wave sensor includes a delay line having a launching transducer and a receiving transducer, each coupled to the propagation medium. The launching transducer converts an electrical signal into a mechanical motion in the propagation medium to generate Lamb waves in the medium. The receiving transducer receives the Lamb waves and produces an electrical signal representative of the mechanical Lamb wave motion along the propagation medium or membrane.

The delay line form may also include a feedback path leading from the receiving transducer back to the launching transducer, having a feedback amplifier, for amplifying the signal produced by the receiving transducer. When sufficient gain is provided by the feedback amplifier, the device forms a feedback oscillator that will oscillate at the frequency of the Lamb waves propagating along the propagation medium.

Also, since semiconductor microfabrication materials and techniques can be employed in producing the membrane, the amplifier can be formed integrally with the propagation medium on a common substrate in, or as a part of, an integrated circuit chip.

In the feedback-oscillator embodiment of the Lamb-wave sensor, the measuring means may be a frequency counter which provides a reading of the oscillation frequency. As a measurand changes the propagation characteristics of the propagation medium or membrane, the oscillation frequency changes. Thus, the oscillation frequency indicates the change in and the value of the particular measurand.

In another form, the delay line is operated as a passive device rather than as an oscillator. In this form, a voltage source supplies the launching transducer, and the receiving transducer is connected to a suitable measuring instrument to determine the relationship between the output and the input signals of the delay line.

Where the delay line structure is operated as a passive device, the measuring means includes a signal amplitude measuring means for measuring the insertion loss of the delay line. This loss depends on the transducer efficiency and the amplitude loss of the Lamb wave as it propagates along the propagation medium. The measuring means may also include means for measuring the phase shift of the Lamb wave as it travels along the propagation medium.

The Lamb-wave sensor of the invention may also be operated as a active or passive one-port device, in which case a single transducer is coupled to the propagation medium. In the passive form, the single transducer is connected to a measuring circuit that determines its input impedance as a function of frequency. In the active one-port embodiment, the transducer is connected into an oscillator circuit where it is the frequency-determining element.

The Lamb waves in this invention have a velocity between 100 and 10,000 (meters per second), as compared with the velocity of 3,000 to 6,000 m/s for SAWs. Also, whereas the SAWs have only a single mode of wave propagation, this mode being non-dispersive, and whereas the Toda voltage sensor couples only to symmetric Lamb wave modes, the Lamb waves of the present sensor have many modes of propagation, some of which are or may be dispersive or antisymmetrical.

An important feature of the present sensor is that the wave velocity of the zeroth-order antisymmetrical Lamb waves in the present propagation medium, is lower than the velocity of sound through most fluids. Therefore, in this mode of propagation, the Lamb waves propagating along the propagation medium or membrane cannot radiate energy into a surrounding fluid. Thus, the sensor may be operated while immersed in fluids. This is in contrast to SAW sensors, in which SAW velocities are higher than the velocity of sound through most fluids, a characteristic which renders typical SAW sensors inappropriate for operation while immersed in fluids.

The present sensor may be coated with materials of low shear modulus (compared to that of the propagation medium). Provided the shear modulus of this overlayer is sufficiently low, little acoustic energy is coupled into the overlayer. This phenomenon has been theoretically and experimentally verified. For example, theory predicts that for a 2-micron thick plate of silicon nitride (shear modulus $1.2 \times 10^{11}$ pascals) there is little change, relative to a water-loaded plate, in the velocity or attenuation of a Lamb wave with 100 micron wavelength, so long as the shear modulus of the overlay is less than about $10^6$ pascals. Many gels satisfy this condition. For the purpose of this specification the terms "low shear modulus material" and "gel" will be used to connote any material that has sufficiently low shear modulus at the frequency of the Lamb wave such that the Lamb wave may propagate without excessive loss.

The Lamb-wave sensor of this invention may operate in a frequency range of approximately 1 to 200 MHz. By contrast, the SAW sensors operate in a frequency range of 10 to 2,000 MHz. The lower-frequency operation of sensors pursuant to this invention is much more convenient in terms of the costs of associated electronic equipment, such as frequency counters and feedback amplifiers, for example.

The novel sensor of this invention can be used in many different sensor applications. For example, it may be used as a microphone, a biosensor, a chemical vapor or gas detector, an accelerometer, a manometer or other pressure-measuring device, a densitometer, a radiometer, or a thermometer.

As an example, consider the use of the device as a manometer to determine gas pressure. When exposed to a steady pressure on both sides of the propagation medium, the sensor of this invention produces a constant-frequency output having a typical value around five megahertz. When the pressure on one side of the propagation medium rises, the output frequency rises monotonically. In one experimental sensor tested, the frequency shifted 0.65 Hz per microbar. This compares very favorably with a prior-art SAW pressure sensor whose output may also be a changing frequency, for the device of the present invention is sixteen times more sensitive, while operating at a frequency about twenty-three times lower than that of the SAW device.

Also, where the sensor forms an oscillator, the oscillator frequency can be stable to less than one part in one million. Thus, in the pressure-sensor example, the device can detect pressure changes as small as a few microbars (millionths of atmospheric pressure).

The invention can also be configured to measure a pressure applied to both sides of the propagation medium or membrane. Pressure applied to the membrane in this fashion will affect the loading of the propagating Lamb wave and may have both dissipative and velocity effects on the wave. However, as mentioned earlier, where the phase velocity of the Lamb wave in the membrane is smaller than the sound wave velocity in the fluid being measured, no wave energy will be radiated to the fluid, and there will be no dissipative effect. The requisite low antisymmetric wave velocity can be achieved by choosing an appropriately low ratio of membrane thickness to wavelength and a low value of in-plane tension.

The dimensions of the sensor can be adjusted so that the center frequency of its antisymmetric mode lies anywhere from 1 MHz to as much as 100 MHz. The range of operating pressure for the device can likewise be adjusted by scaling the device dimensions.

Where the sensor is employed as a microphone, the membrane produces an output that varies about a fixed (carrier) frequency in response to an incident sound wave. Specific applications include using the device as a sound pickup in a gas or liquid, or through solid contact for vibration monitoring.

The new sensor can also be employed in chemical sensing applications. For example, when the device absorbs vapors or gases from the atmosphere in a film deposited on the membrane, the output frequency changes. Simulations indicate that the device is at least an order of magnitude more sensitive than a SAW vapor sensor operating at the same wavelength, for example at 141 micrometers.

The sensor has superior gravimetric sensitivity, and can operate while in contact with a liquid such as water. Thus, as noted, its use as a biosensor is very significant.

For example, the membrane can be pre-coated with antibody molecules, so that the frequency of the device changes upon immersion in a liquid that contains the corresponding antigen. Antigen-antibody attachment at the surface of the propagation medium acts to alter the wave velocity causing the oscillation frequency to change in the delay line oscillator form. Also, the membrane may be made of a porous and permeable material, allowing the coating of a greater surface area and also allowing the antigen-containing liquid to be flowed through the membrane, in order to speed up the antigen-antibody attachment. Other biological interactions may also be sensed, and additional applications include immunoassay, clinical laboratory testing, in vivo biomedical monitoring, and biomedical research.

Practical biosensors must detect the desired substance while in the presence of many other substances — cells, proteins, etc. Interaction of the sensor with these other substances may mask the desired interaction. In fact, in gravimetric ultrasonic sensors, the attachment of these competing substances to the sensor surface may cause a mass-loading response much larger than that caused by the desired test substance. For example, glucose can be detected gravimetrically through the use of an ultrasonic wave crystal that is coated with the enzyme hexokinase: when glucose molecules are interacting with the enzyme, the crystal is mass-loaded and its oscillation frequency drops. But if the glucose were presented to the crystal together with blood cells and plasma, as in the human cardiovascular system, the non-specific binding of those other cells and molecules onto the sensor could entirely mask the glucose-enzyme mass-loading effect.

If, however, the propagation medium of the new sensor of the present invention is coated with a layer of a suitable gel, the gel can screen out massive cells and molecules while detecting smaller molecules. Such a biosensor may serve as an in vivo glucose sensor, for example, for use in a closed-loop insulin delivery system for diabetics. Other applications include use in pressure sensing, in vapor sensing with an adverse ambient, in the monitoring of cell growth, and as a Lamb-wave detector in gel chromatography systems.

BRIEF DESCRIPTION OF THE DRAWINGS

FIG. 1 is a greatly enlarged schematic cross-sectional view of a Lamb wave sensor embodying the principles of the invention, drawn to an exaggerated vertical scale.

FIG. 2 is a further enlarged view of a portion of the membrane of FIG. 1.

FIG. 2a is an enlarged view of an alternative design of a portion of the membrane of FIG. 1.

FIG. 3 is an enlarged view similar to FIG. 2, but showing a portion of a membrane that includes a protective coating.

FIG 4 is a schematic cross-sectional view a sensor having only a partial ground plane.

FIG. 5 is a schematic cross-sectional view a membrane that consists entirely of a piezoelectric material.

FIG. 6 is a somewhat schematic top plan view of the sensor shown FIG. 1, showing the transducer arrangement.

FIG. 6a is a schematic top plan view of a Lamb-wave sensor having transducers that extend the full width of the propagation medium.

FIG. 7 is a schematic representation of a selective Lamb wave sensor that includes a reference oscillator.

FIG. 8 is a schematic representation of a Lamb-wave sensor having an output that is compensated to exclude slowly-varying phenomena.

FIG. 9 is a schematic cross-sectional view of an alternative embodiment of a sensor according to the invention.

FIG. 10 is a schematic cross-sectional view of a passive one-port sensor embodying the principles of the invention, drawn to an exaggerated vertical scale.

FIG. 11 is a schematic cross-sectional view of an active one-port form of the sensor of this invention.

FIG. 11a is a schematic cross-sectional view of a plate-wave resonator with distributed reflectors according to the invention.

FIG. 11b is a schematic top plan view of a Lamb-wave structure including a thermoelastic transducer.

FIG. 11c is a schematic cross-sectional view of an optical means for thermoacoustic generation of Lamb waves.

FIG. 12 is an enlarged schematic view of another transducer arrangement which may be used pursuant to the invention, where the membrane is coated with a gel material.

FIG. 13 is a schematic representation of another form of the sensor of FIG. 12.

FIG. 14 is a schematic representation of a gel-coated sensor having a selective sorptive coating.

FIG. 15 is a schematic view of another form of the invention using a gel-coating on both sides of a sensor.

FIG. 16 is a schematic view of a sensor according to the invention, having a porous and permeable membrane.

FIG. 17 is a schematic view of a membrane device on which have been formed electrodes for the electrophoretic separation of molecules.

FIG. 18 is a schematic view of a membrane device on which a resistive heater has been formed so that the temperature of the membrane region can be altered electrically.

FIG. 19 is a schematic view of a membrane device in which cells or organisms are contained in the gel.

DESCRIPTION OF THE PREFERRED EMBODIMENTS

FIG. 1 illustrates one form of a Lamb wave ultrasonic sensor 20 embodying the principles of the invention. The sensor 20 includes a substrate 21 that supports a propagation medium or membrane 22. A launching transducer 23 and a receiving transducer 24 are located on the propagation medium at spaced-apart locations. Separated from the propagation medium 22, a feedback amplifier 25 is connected in a feedback path 26 between the receiving and launching transducers, and a frequency counter 27 is connected to the output of the feedback amplifier 25.

A preferred form of the propagation medium or membrane 22 is shown in detail in FIG. 2. The membrane 22 is a planar sheet of material comprising a film or base layer 30 of nonconductive or semiconductive base material, a film 31 of conductive material, and a thin film 32 of piezoelectric material. A layer 33 of conductive material representing a portion of a transducer structure is also shown deposited on the upper surface of the membrane 22. The propagation medium 22 shown in FIG. 2 may be formed, pursuant to the invention, having an inherent tensile stress, as may the other propagation medium forms of the invention. This inherent tensile stress may be used to advantage in sensing applications and also helps in maintaining the true planar form of the propagation medium.

The base layer 30 may be made of silicon nitride having a thickness of approximately 2.0 microns. The layers 31 and 33 may both be aluminum, each approximately 0.3 microns in thickness, the layer 31 forming a ground plane for the transducers and the material 33 forming the transducer electrodes. The piezoelectric layer 32 may preferably comprise zinc oxide having a thickness of approximately 0.7 microns.

As an alternative to the structure of FIG. 2, that of FIG. 2a may be used in which the layers 33' that are a portion of the transducer structure 22' are deposited onto film or base layer 30', the layers 33' being covered with piezoelectric layer 32' and ground plane 31'. An advantage of this inside-out structure is that the ground plane 31' on its upper surface provides electrical shielding against electric fields present where the device is to be used and which might interfere with device operation.

As shown in FIG. 3, the propagation medium or membrane may include a protective coating 34. For example, the protective coating 34 may comprise a thin layer of polytetrafluoroethylene (Teflon) that prevents corrosion of electrodes when the sensor is immersed in liquids or is operated in corrosive environments. The protective coating 34 may alternatively be a thin silicone coating to prevent blood coagulation at the sensor's surface, when it is used for in vivo monitoring in the cardiovascular system.

Another alternative propagation medium 40 is shown in FIG. 4. In this form of the sensor, there is no ground plane along at least a portion of the propagation medium between two transducer structures 41 and 42. Rather, a ground plane 43 is restricted to the area of the transducers 41 and 42. With this propagation medium 40, the electric fields generated by the piezoelectric material 46 can extend into a dielectric liquid 45 on the other side of the silicon nitride layer 44. Thus, the sensor employing this propagation medium 40 can respond to the dielectric and conducting properties of the liquid 45.

In FIG. 5 the propagation medium or membrane consists entirely of a piezoelectric film 47. Transducers 48 and 49, shown schematically, are coupled to the piezoelectric film 47 for generating both symmetrical and antisymmetrical Lamb wave modes. In this case the film 47 may be a piezoelectric polymer such as polyvinyl-fluoride.

FIG. 6 shows the preferred transducer structure in plan. Both the launching and the receiving transducers 23 and 24 respectively, are interdigital finger transducers deposited directly on the propagation medium 22. The launching transducer 23 comprises two electrodes 36 and 37, and the receiving transducer 24 comprises two electrodes 38 and 39.

In operation of the embodiment illustrated in FIGS. 1, 2, and 6, the Lamb waves are launched at the launching transducer 23, with the transducer electrodes 36 and 37 being driven differentially with respect to the ground plane 31. Thus, an alternating electrical field is created between each electrode finger F and the ground plane 31 across the piezoelectric layer 32. The piezoelectric layer 32 is deformed in response to the alternating field and generates a Lamb wave, which then propagates along the propagation medium 22. The wavelength of the Lamb wave so generated is approximately equal to period P of the electrode fingers or an odd integral fraction of P, such as P/3 or P/5, for example.

The transducer electrodes 36", 37", 38" and 39" may extend entirely across the width of the propagation medium 22" as depicted in FIG. 6a. This arrangement would maximize coupling of electrical energy into acoustic waves and would also maximize the area over which changes in the propagation medium may be sensed.

As an alternative, transducer electrodes 36 and 37 may be connected together and driven by an electrical source connected between them and the nearby ground plane. In this case, the wavelength of the Lamb wave so generated is approximately equal to the period P of the electrode fingers or to any integral fraction of P, such as P/2, P/3, or P/4, for example. Or, one may elect to drive only one transducer electrode, such as 36, in which case operation, at somewhat reduced efficiency, occurs at a wavelength approximately equal to the period $P_{36}$ of the electrode 36, or to any integral fraction of $P_{36}$, such as $P_{36}/2$, $P_{36}/3$, and so on. $P_{36}$ is equal to the distance between centers of adjacent fingers of transducer electrodes 36. Further, one may elect to drive transducer electrodes 36 and 37 with respect to the ground plane with two independent electrical sources that produce waves of different wavelengths. In this case, the wavelengths of the waves produced are approximately $P_{36}$, $P_{36}/2$, $P_{36}/3$, etc. and $P_{37}$, $P_{37}/2$, $P_{37}/3$, etc., where $P_{37}$ is the period of transducer electrodes 37. The use of additional transducing structures that produce additional waves that propagate simultaneously and independently on wave propagation structure 22 is also in the spirit of this invention, as is also the use of other transducing phenomena, such as electrostriction to produce the waves.

In order to generate antisymmetric mode Lamb waves in a propagation medium, some asymmetry is required. An asymmetrical membrane or propagation medium is one that does not have perfect symmetry with respect to an imaginary plane that is parallel to and equidistantly spaced from the two outer surfaces of the membrane. From such an asymmetrical structure, both antisymmetric and symmetric mode Lamb waves may be generated.

In the membrane embodiments illustrated in FIGS. 2, 3, and 4, asymmetry is provided by the different thicknesses of the membrane constituent layers. In the membrane shown in FIG. 5, which has only a single layer 47, of piezoelectric material, asymmetry is provided by having no ground plane electrode. If a ground plane electrode is used in a single layer membrane, asymmetry may be provided by making the ground plane from a material having a different weight from the transducer electrode material, or by making the ground plane with a different thickness.

The Lamb waves launched at the transducer 23 propagate along the propagation medium or membrane 22 to the receiving transducer 24 and cause a deformation of the piezoelectric layer 32 at the receiving transducer 24. This wave-induced deformation of the piezoelectric layer 32 causes an electrical signal at the transducer 24, which is representative of the Lamb wave at that point.

Waves naturally launched by the transducer 23 in a direction away from the transducer 24 are prevented from interfering with sensor operation by angled ends 28 that reflect these unwanted waves, so that their wavefronts are no longer parallel to the electrode fingers of the transducers. Also, the Lamb waves that travel past the transducer 24 are reflected similarly at angled ends 29 to prevent their reflections from actuating the transducers. Alternatively, a dissipative absorptive material, such as a wax, may be placed on the membrane 22 beyond and to the right and left of the transducers 23 and 24, respectively, to prevent wave reflections.

The signal received at the transducer 24 is fed back along the feedback path 26 to the amplifier 25, where the signal is amplified sufficiently to sustain oscillation. The amplified signal is then fed back to the launching transducer 23. The transducers 23 and 24, the propagation medium 22, and the feedback amplifier 25 thus form an oscillator that operates at the frequency of the Lamb waves travelling through the propagation medium 22. For a given Lamb wave mode, such as the zeroth-order antisymmetric mode, the frequency response of the amplifier gain determines at which of its possible frequencies the device will oscillate.

The frequency counter 27 is preferably connected to the feedback path 26 at the output of the amplifier 25, where the signal representing the Lamb wave is greatest. The frequency counter 27 includes a display (not shown) that provides a readout of the oscillation frequency.

The Lamb-wave sensor illustrated in FIG. 1, 2, and 6 senses a measurand that alters the characteristics of the material which makes up the propagation medium or membrane 22. These material characteristics include elastic stiffness, density, tension, thickness, length between the transducers, piezoelectric stiffening, and type of loading, both reactive and dissipative. A change in the membrane material characteristics, in turn, affects characteristics of the Lamb waves propagating along the membrane 22. These latter characteristics are monitored to provide an indication of the measurand value.

The sensor embodiment illustrated in FIGS. 1, 2, and 6 can be used as a microphone, since an airborne sound wave impinging on the membrane 22 will strain the membrane, causing the Lamb wave phase velocity to become time-varying and producing a modulation of the oscillator frequency. The microphone output will be a frequency-modulated voltage with information about the impinging sound wave carried in its sidebands.

Lamb wave phase velocity can be altered by physical changes that occur in a sensitive coating film on the membrane 22 when the coating interacts with chemical or biological species carried in a liquid. Also, zeroth-order antisymmetric Lamb waves have phase velocities low enough to permit their use while in contact with a fluid, without loss of wave energy to the fluid. Therefore, the sensor 20 can be operated while immersed in a fluid, an ability required for many chemical and biological sensing applications but difficult to achieve in SAW devices.

Since the Lamb-wave device responds to changes of membrane tension, surface loading, and changes in transducer dimensions, it is suited to a number of mechanical applications. A force applied to the membrane directly or to the substrate, strains the membrane and causes a change in oscillator frequency. Thus, the sensor could be employed as a scale for weighing very small masses. Also, since surface loading from the deposition of material on the membrane surface causes a response, the sensor can be employed as a deposition monitor for use in an evaporation or sputtering system, for example.

Response to gas or liquid pressure can be realized in two ways. If the propagation medium or membrane 22 is subjected to unequal pressures on its two sides, strain of the membrane will cause an oscillator frequency to change. If both sides of the membrane 22 are subject to the same pressure, the membrane tension will be constant, but loading of the propagating Lamb wave will depend upon the pressure, and so produce a sensor response.

Loading one or both sides of the membrane 22 with a fluid can cause large velocity changes and oscillator frequency shifts. Analysis shows that the magnitude of the change depends primarily upon the density of the fluid, the sound velocity in the fluid having a somewhat smaller effect. Thus, density and mass of the loading fluid may also be measured with the device illustrated in FIGS. 1-6.

Temperature has several effects on the wave propagation characteristics of the membrane or propagation medium 22. Temperature affects the elastic stiffness, tension, and density of the membrane 22, as well as the length of the membrane 22 between transducers. Thus, the device illustrated in FIGS. 1-6 can also be used to measure temperature with great sensitivity.

The sensitivity to temperature also makes it possible to use the sensor as a radiometer. As a radiometer, the incident radiation heats the membrane to cause the response. Also, the response of the sensor as a radiometer can be increased by the addition on the membrane of a layer of black material, such as graphite, which strongly absorbs radiant energy.

The Lamb-wave sensor illustrated in FIGS. 1, 2, and 6 may be formed on a silicon wafer by depositing LPCVD silicon nitride uniformly over a wafer (not shown) and then etching away the silicon from beneath the nitride layer 30. The LPCVD silicon nitride can be deposited at 835° C. in a 5 to 1 gas ratio of dichlorosilane and ammonia, to obtain a low stress film suitable for fabricating membranes. Deposition time may be approximately 5 hours to obtain a 2 micron-thick film. Using a two-sided alignment technique, windows may be patterned in the backside nitride (not shown) by plasma etching. Silicon may then be etched away, using the nitride as an etch mask, with ethylenediamine, pyrocatechol and water (EDPW) to leave a 2 micron-thick nitride membrane on the front side.

Following formation of the thin plate 30 of silicon nitride, zinc oxide piezoelectric material 32 may be sputtered onto a 0.30 micron-thick evaporated aluminum ground plane 31. The 0.7 microns of zinc oxide may be deposited by RF planar magnetron sputtering. Onto this layer 32 of zinc oxide, 0.30 microns of aluminum may be evaporated, using the marks generated during the two-sided alignment step to pattern interdigital transducers 23 and 24 centered on the membrane 22. For etching the aluminum, a solution of KOH, $K_3Fe(CN)_6$ and water (1 g:10 g:100 ml) may be used; this solution does not etch zinc oxide.

The feedback amplifier 25 used in the embodiment illustrated in FIG. 1 may comprise two cascaded LM733 differential video amplifiers. The device may be driven untuned, and an amplifier gain of approximately 40 dB is necessary to sustain oscillation.

Alternatively, the feedback amplifier 25 may be formed integrally with the propagation medium on a common silicon wafer substrate. Semiconductor microfabrication techniques may allow other circuitry to be included on the substrate material, such as mixers, and frequency counters. Drivers for sending signals off-chip for storage, interpretation, and display may also be formed on a substrate common with the propagation medium. A microprocessor and memory for converting frequencies into relevant physical, chemical, or biological parameters may also be included on the same base material.

The frequency can be measured with a frequency counter 27. A typical frequency counter is the Hewlett-Packard Universal Counter, Model 5316A, which determines the frequency of an AC voltage from the number of polarity reversals that occur in an accurately known time interval. Such a counter can determine frequencies to a precision of 1 Hz or better, and can output a binary indication of the frequency for transmission to auxiliary digital equipment for storage and processing.

For measuring the frequency of minimum insertion loss, RF pulses of 0.5–2 microsecond duration may be applied to one transducer 23, and the RF frequency can be tuned to maximize the received signal amplitude from the second transducer 24. The velocity of maximum transducer coupling is found by multiplying this frequency by the acoustic wavelength. Using the same apparatus, the group delay times could be measured, and hence group velocity.

As with other ultrasonic sensors, the Lamb-wave sensor of the invention encounters the problem of providing a response selective to the particular measurand of interest. The selective sensor embodiment 50 shown in FIG. 7, employs a reference device 51 and an active device 52, the active device 52 being exposed to all measurands that act on the sensor and the reference device 51 being exposed to all such measurands except the one of interest. The value of the measurand of interest is found by observing the difference in the active and reference device outputs.

The sensor 50 in FIG. 7 is a pressure sensor in an environment where temperature may be changing. The reference device 51 includes a Lamb-wave sensor element 53a enclosed in an inflexible enclosure 54. The active device 52 includes a Lamb-wave sensor element 53b, which is identical to the sensor element 53a, but in a flexible enclosure 55. Both enclosures 54 and 55 are filled with an inert filler gas 56. In the illustrated embodiment, the sensor elements 53a and 53b are delay line devices such as the embodiment illustrated in FIG. 1. The outputs from the two sensor elements 53a and 53b are conducted through feed-through leads 57a and 57b, respectively, and compared in a circuit 58. The circuit 58 includes a frequency mixer and a frequency counter 60 that measures the difference between the oscillation frequencies of the active device 52 and the reference device 51. The circuit 58 also provides on output 59 of this frequency difference for any auxiliary equipment. As both devices are affected equally by temperature changes, only the different responses to pressure affects the difference frequency from circuit 58.

The sensor embodiment illustrated schematically in FIG. 8 avoids problems with slowly-varying frequency changes such as those caused by ambient temperature changes. The sensor includes a sensor element 61 which may be of the type illustrated in FIG. 1. However, interposed between the sensor element 61 and the voltmeter 62 is a phase-locked loop circuit 63, and a high-pass filter 66. One possible embodiment of the high-pass filter 66 is an RC filter comprising a capacitor 64 and a resistor 65. Slow changes in the phase-locked loop 63 output, caused by its input signal drifting with temperature, are blocked by the filter 66, so that the signal to the voltmeter 62 is temperature-compensated. Other slowly-varying conditions are also compensated for.

Other solutions to the problem of providing selective response include packaging to exclude unwanted influences, exploiting solubility parameter matching or selective chemical reactions in chemical sensors, employing thermal desorption spectroscopy in vapor or gas sensors, using selective immunological reactions in biosensors, and pattern recognition to obtain a definitive indication from an array of sensors that are only partially selective.

A passive delay line embodiment of the Lamb-wave sensor pursuant to the invention is illustrated in FIG. 9. In this embodiment, a delay line is used having launching and receiving transducers, 71 and 72 respectively, separated on a propagation medium 70 capable of supporting Lamb waves, similar to the embodiment shown in FIG. 1. A variable-frequency voltage source 73 activates the launching transducer 71 and also supplies a reference voltage signal $V_R$ to an amplitude and phase comparator 74, which may be a vector voltmeter, a network analyzer, or an instrument that measures time delay and signal magnitudes. Lamb waves activating the receiving transducer 72 cause an electrical output $V_A$ that is also supplied to the comparator 74. The characteristics of the propagation medium, and hence the measurands, which affect the medium, can be determined from the comparator outputs 75 and 76.

An alternative embodiment 80 of the invention is illustrated in FIG. 10 and instead of a delay line employs a one-port device 81 operated as a passive element. A launching transducer 84 is activated by a variable frequency voltage source 85, through a measuring circuit 86. The launching transducer 84 is coupled to the propagation medium 87, having a ground plane 88 connected to ground. The circuit 86 measures the current and voltage supplied to the transducer 84, while the frequency varies in a known fashion. The variations of the transducer current and voltage with frequency of the voltage source, are sensitively affected by the characteristics of the propagation medium 87. Therefore, measurand values affecting the propagation medium can be determined from the variations of transducer voltage and current.

In the active one-port embodiment shown in FIG. 11, the transducer 91 is coupled to the propagation medium 93 having a ground plane 94 connected to ground. The transducer 91 is electrically connected to an oscillator circuit 90. Characteristics of the propagation medium 93 determined by a measurand, affect the electrical input impedance of the transducer 91, and thus affect the oscillator frequency measured by the frequency counter 92. Therefore, the value of the measurand can be calculated from the measured frequency.

A variation on the one-port device is the plate-wave resonator illustrated in FIG. 11a. In this embodiment the plate 111 would contain structures 110 that reflect the plate waves. Such reflectors might be "distributed reflectors" consisting of periodic perturbations to the plate that cause variations in the velocity of acoustic waves propagating thereon. Distributed reflectors could consist of strips of material deposited on the plate to increase the mass per unit area of the plate, of periodic grooves etched into the plate, or of strips of a conductive material to cause a local reduction of "piezoelectric stiffening". Alternatively, the edges of the plate may act as reflectors. In each case, the plate waves would bounce back and forth between two or more reflectors to form a resonant cavity. The resonator may have one or more transducers 109 to launch and receive acoustic waves. The plate-wave resonator could be used in either passive or active embodiments as illustrated in FIGS. 10 and 11. The spacing and periodicity of the reflectors, characteristics of the propagation medium 111, and properties of the surrounding environment determine the resonant frequency of the resonator.

Thermoelastic coupling to Lamb waves has been described by Richard M. White in "Thermoelastic Coupling to Lamb Waves," Proc. 1986 Ultrasonics Symposium, pp. 411, 415, 1986. The efficiency of thermoelastic bulk wave generation can be increased by mechanically constraining one surface of semi-infinite solids. In the present invention, the gel may act to constrain one surface of the plate, increasing the efficiency of Lamb wave generation. An electrical means of thermoelastic Lamb-wave generation is illustrated in FIG. 11b. Here, the transducer fingers 132 are made from a resistive material such as polycrystalline silicone or nickel-chromium (nichrome). A time-varying electric current is passed through the transducer fingers to heat the plate 22 beneath the transducer 131. Local thermal expansion of the plate generates a Lamb wave. An optical means for thermoelastic Lamb-wave generation is depicted in FIG. 11c. A temporally-modulated light source 134 and mask 133 produce periodic heating of plate 135.

As shown in FIG. 12, the propagation medium or membrane 22 may include a gel coating 100. The thickness of the coating may exceed that thickness of the membrane and the wavelength of the Lamb waves.

It has been observed that it may be difficult to define a gel though it is easy to recognize one. A recent book on the subject ("Physical Networks: Polymers and Gels", W. Burchard and S. B. Ross-Murphy, Editors, Elsevier Applied Science, London, 1990) gives several definitions of a gel: First, "a coherent system of at least two components, which exhibits mechanical properties characteristic of a solid, where both the dispersed component and the dispersion medium extend themselves continuously throughout the whole system" (page 15). Second, "a substantially diluted system which exhibits no steady state flow" (page 16). Among the gels that have been used as coatings on the device shown schematically in FIG. 12 are gelatin, agar, polyacrylamide, and polyvinylalcohol.

As illustrated in FIG. 13, gel coating 100 may have planar top surface onto which pressure or discrete forces can be applied to cause sensor response to those physical measurands. A protective coating 34 is shown on the gel coating to give it greater mechanical rigidity, prevent puncture by objects applying force, and/or to seal it to prevent absorption of gases or moisture from the surrounding atmosphere. The gel coating will also eliminate certain unwanted responses from the device.

Use of the gel coating to prevent non-specific binding from causing an unwanted gravimetric response in a biosensor is illustrated in FIG. 14. The gel-coated sensor is shown exposed to a biological fluid 102 containing a variety of large cells 104 together with small molecules 106. The small molecules can diffuse rapidly through the gel 100 and bind to a suitable selective sorptive coating 108 on membrane 22. The liquid shown might represent blood, the small circles glucose molecules (seven angstroms across), and the other shapes cells and large protein molecules (diameters from 50 angstroms to many microns).

The layer 108 of sorptive material may be deposited on one surface of base propagation medium or membrane 22 to form part of the propagation medium. Transducers 23 and 24 are located on the opposite surface.

The sorptive coating in this case might be the enzyme hexokinase, which acts in the human body as a catalyst for the reaction of glucose with ATP (adenosine triphosphate) to form glucose 6-phosphate. It is known that a gravimetric response to glucose can be obtained with a bulk-wave piezoelectric crystal coated with a thin layer of hexokinase-containing gel, and that hexokinase retains its catalytic ability when dispersed in poly-(acrylamide) gel. Thus, the sensor of the present invention should function well.

Alternatively, a sorptive material, such as the enzyme hexokinase, may be dispersed throughout the gel.

In the structure shown in FIG. 14, the ultrasonic wave causes an evanescent disturbance in the vicinity of the membrane. The spatial extent of this disturbance is roughly equal to the wavelength divided by $2\pi$, a distance typically ranging from five to sixteen microns. The large cells and molecules lying on the upper surface of the gel will not be detected if the gel thickness is made somewhat greater than this distance.

As noted, the gel overlayer could be used as a filter that prevents large components, such as blood cells, from activating the sensor (because its sensitive region is quite close to the membrane) while letting smaller components, such as salts, glucose, etc., diffuse to the membrane and cause a stiffness, mass, density or viscosity change that is detected there. The diffusion of a salt/water solution into a water-based gel produces a diffusion characteristic (that yields a sensible diffusion constant) showing a measurement use for the sensor.

The use of a selective absorber on the membrane and the gel coating produces a filter function and a selective response. This could permit fabrication of a glucose sensor, for example, that does not require separate filtering of the large components of whole blood.

For reasons of economy, the addition of sorptive coatings may be done at wafer scale when semiconductor microfabrication techniques are employed in fabricating the sensors. However, membranes having different sorptive films may be desired in a single wafer. Such different sorptive materials may be deposited by repetitive photomasking, or preferably, with an ink-jet printing process. In the preferred case, an ink-jet printing head having multiple jets may have each jet independently supplied with a different sorptive material, usually a polymeric liquid. The ink-jet head, translated near and in a parallel plane with the wafer, may deposit controlled amounts of material in well defined locations. Thus, different sorptive materials may be deposited on membranes made from a single wafer or substrate material.

FIG. 15 shows use of the gel coating on both sides of a delay line to protect it from harmful substances in the ambient atmosphere around it.

The gel coating may also be placed over a porous and permeable membrane 22', as shown in FIG. 16. The process of putting the gel on such a membrane could be done with the aid of surface tension, which would keep the gel solution from flowing through holes 110 when first applied to one side of the membrane. This would permit use of the gel as described above, for example, with one component from a fluid diffusing through the gel to the membrane, with the ability to quickly change chemical conditions near the membrane by suddenly flowing in some fluid, on the second or opposite side of the membrane, that would change the chemical conditions in the gel near the membrane. Such a process may help to increase chemical selectivity of the sensor in detecting which of certain possible substances were present (any of them might cause a given gravimetric response, but changing chemical conditions via the fluid introduced from the second side of the membrane might change the binding or retention of one substance but not another).

This may also be a way to introduce a desirably selective binding layer into the gel just near the membrane. For instance, a gel solution may be applied to the first side of the membrane and allowed to set. A solution of a binding material may then be put on the second side of the membrane, and be allowed to move a small distance into the gel. As an example, an undoped gel may be used and a glucose-binding enzyme, such as hexokinase, can be introduced on the second side of the membrane.

Certain gels, such as siloxane gels, have a swelling property that depends on the pH of the fluid that they are exposed to. With such a gel on the sensor's membrane, the large change of gel density near the membrane can be used to indicate pH changes with very high resolution.

Where a gel layer is deposited directly on a porous or permeable, sensor membrane according to this invention, the surface area of the membrane, and thus the gel material, is increased. That is, the gel adheres to the pore walls to provide a greater surface area. A membrane according to this invention may be made porous by particle track etching either completely through its thickness to provide porosity and permeability, or through only a portion of its thickness to provide only porosity. Other sensor membrane embodiments may also be made porous, or both porous and permeable, by particle track etching.

Various gels have been used to form coating 100. For example, unflavored gelatin, flavored gelatin (such as Black Cherry Jello), and a 1% dispersion of agar in water (a common constituent of culture medium) are suitable gel materials. As expected, when the heated liquid solution of gelatin or agarose was placed on the sensor, the wave velocity dropped as is observed with pure liquids such as water or methanol. Once the gel set, contrary to what might have first been supposed, the wave velocity barely changed, even though the gel material loading the delay line became relatively solid. This meant that the ultrasonic wave energy was still traveling primarily in the few-micrometer-thick membrane. Thus, the sensor could still exhibit gravimetric response. Other gels such as polyacrylamide, commonly used in chromatography, should behave similarly.

Thus, water-based gels, such as gelatin, agar, polyacrylamide, polyvinylalcohol in the $\frac{1}{2}$ to 1% concentration range, can be allowed to set on the sensor of the present invention without causing either a large shift of elastic wave velocity, as would a very stiff overlayer, or a large increase in elastic wave attenuation, which might result if an overlayer having near-solid properties were applied.

One application is to electrophoresis on the sensor. Specifically, various proteins, DNA fragments, etc. could be moved by applying an electric field in a polyacrylamide gel (typically used for electrophoresis). Detection of the presence of a macromolecule moved by the electric field may be by a change of mass loading (gravimetric detection with Lamb-wave device), by customary optical means (looking through a transparent region of the membrane), etc. Electrophoresis may be done parallel to the plane of the membrane (electrodes on the membrane, separated by a small distance laterally) or perpendicular to the membrane (using as electrodes a conducting coating on the membrane itself and one at the surface of the gel or in the electrolyte outside the gel). In the latter case, a change in density would be detected as components moved through the gel to the sensitive region near the membrane.

By applying suitable potentials to left and right electrodes 114 and 116, respectively, on the membrane and on the gel's surface or in a liquid 115 that contacts the gel, as shown in FIG. 17, one could force molecules into the gel from the liquid or remove them from the gel. It would further be possible to inject molecules into the gel (with a perpendicularly applied electric field by upper and lower injection electrodes 118 and 120, respectively), separate molecules having different sizes by conventional electrophoresis in the gel (with an electric field applied parallel to the membrane), and then remove a particular group of molecules from the gel and into a liquid in contact with the gel (with another perpendicularly applied electric field set up by upper and lower removal electrodes 122 and 124, respectively, set up at an electrode "downstream" from where the molecules entered the gel).

Lamb waves can be used to pump fluids. It may be possible to use this effect to drive the liquid phase within a gel through the gel matrix. This might be useful for gel chromatography wherein chemicals are separated by the ease with which they pass through a gel. The addition of Lamb waves may speed the separation or may be combined with the electrophoreses described above to realize more sophisticated separations of chemicals.

Note that some gels can be removed (and even replaced later) mechanically, as with tweezers. The gel taken from the sensor looks like a soft contact lens. Presumably, gels could also be removed by heating of the membrane; such heating may conveniently be caused by passing current through a resistive element 112 (for example, made of polysilicon, aluminum, platinum, nickel chromium, etc.) made integrally with the membrane, as shown in FIG. 18. Such heating may additionally be used to stabilize the temperature of the membrane region by supplying to it a controlled heating current. The resistance of the heater or resistive element, which might be made of polycrystalline silicon, provides an indication of the heater's temperature and so may be used in a temperature-controlled feedback loop to maintain a stable membrane-region temperature. Another use for this heater is to vary the temperature in a controlled way over many degrees, causing the release of molecules that have been sorbed in layer 108. Monitoring the temperatures at which changes of sensor frequency occur could then provide information about the types of molecules that had been sorbed.

The gel 100 may contain cells or living organisms 130, as illustrated in FIG. 19. For example, yeast cells have been entrapped in an alginate gel on a Lamb wave sensor. The gel was perfused with a glucose solution which the yeast metabolized to ethyl alcohol. The density decrease due to glucose metabolism and ethanol production was sensed as a rise in the oscillation frequency of the sensor. This configuration may be generally useful for monitoring the growth or metabolic rate of many living cells or tissues.

A gel layer could also be used to couple the membrane 22 to a solid support. This support could provide mechanical rigidity to the sensor and could also act as a heat sink or source to regulate the temperature of the plate.

As discussed, the gel-coating does not adversely affect the sensor's operation. As a typical water-based gel sets while in contact with the membrane, there is virtually no change in either the ultrasonic wave velocity or attenuation.

The peak transmission of RF energy through a sensor in air may occur at 7.7 MHz. Putting a gelatin solution on the delay line reduces the response frequency to about 5.6 MHz. The solution may be heated above the melting point (around 40° C.) and allowed to cool below the gelling point with virtually no change in the frequency or amplitude of the transmission peak. As noted, the gel can be removed from the sensor and replaced physically; the sensor response will nearly regain its original values.

The loading presented by the gel does somewhat reduce the sensitivity of the sensor from that in air, but this reduction is nearly the same as occurs when the sensor contacts liquid for use as a biosensor. Note also that gels such as agarose are biocompatible, leading to the strong possibility of using the sensor in the human body. Incidentally, a tradeoff exists between gel thickness and response time: a thick gel will protect the device better but also increase the time required for molecules to diffuse to the sensing surface or membrane.

The gel-coated sensor may be most useful as a gravimetric biosensor to screen out massive cells and molecules (such as blood cells and proteins) while detecting smaller molecules (such as glucose). Other sensor embodiments in accordance with the principles of the present invention are discussed in the above-identified application Ser. No. 07/467,412, the entire disclosure of which has been incorporated herein by reference.

The above-described embodiments are intended to illustrate the principles of the invention, but not to limit the scope of the invention. Various other embodiments and modifications to those embodiments may be made by those skilled in the art, without departing from the scope of the appended claims.

What is claimed is:

1. An ultrasonic structure comprising:
   a propagation medium comprising a thin planar sheet capable of supporting Lamb waves, said sheet having a thickness very much thinner than the wavelength of the Lamb waves to be propagated thereon, said propagation medium including on a surface thereof a layer of a low shear modulus material; and
   electrical means coupled to the thin planar sheet of said propagation medium for producing Lamb waves in the propagation medium.

2. The structure as recited in claim 1, wherein the electrical means includes means for producing both symmetrical and antisymmetrical Lamb waves in the propagation medium.

3. The structure as recited in claim 2, wherein the propagation medium includes a layer of silicon nitride.

4. The structure as recited in claim 3, wherein the propagation medium includes a layer of piezoelectric material.

5. The structure as recited in claim 1 wherein said sheet has some physical characteristics determined by the value of a measurand acting thereon, said physical characteristics determining the propagation characteristics of Lamb waves to be propagated along the medium; and further including output means on said sheet for producing an electrical signal representative of the determined propagation characteristics of the Lamb waves propagating along the propagation medium, and measuring means for measuring selected characteristics of said electrical signal, whereby when said structure is acted on by a measurand, the physical characteristics of said propagation medium are determined and said electrical signal characteristics are also determined, so that said measuring means indicates the value of the measurand.

6. The structure as recited in claim 5, wherein the output means includes a receiving transducer, coupled to the propagation medium, for producing an electrical signal representative of the Lamb waves propagating along said propagation medium;
   the electrical means includes a launching transducer, coupled to the propagation medium, for generating Lamb waves in the propagation medium;
   a feedback path between the receiving and launching transducers for providing feedback from the receiving transducer to the launching transducer;
   a feedback amplifier in the feedback path for amplifying said electrical signal produced by the receiving transducer and fed back to the launching transducer, the structure forming an oscillator in which Lamb waves are continuously propagated along the propagation medium; and
   the measuring means includes frequency measuring means for measuring the oscillation frequency.

7. The structure as recited in claim 6, including Lamb wave reflecting means for reflecting Lamb waves generated by the launching transducer that propagate in directions away from the receiving transducer, so that the reflected Lamb waves do not produce an output at the receiving transducer.

8. The structure as recited in claim 1 wherein at least a portion of the propagation medium is porous.

9. The structure as recited in claim 8 wherein the porous portion of the propagation medium is also permeable.

10. The structure as recited in claim 1 wherein a layer of sorptive material is disposed between said propagation medium and said layer of low shear modulus material.

11. The structure as recited in claim 1 wherein a sorptive material is dispersed throughout said layer of low shear modulus material.

12. The structure as recited in claim 1 wherein said layer of low shear modulus material is a material selected from the group consisting of agar, gelatin, polyacrylamide, polyvinylalcohol, alginate, and other gels formed from seaweed, siloxanes, polyvinyl chloride gels, pectin, and the glycoprotein-based gel, mucus.

13. The structure as recited in claim 1 wherein the propagation medium includes a means of heating said layer of low shear modulus material.

14. The structure as recited in claim 1 wherein said layer of low shear modulus material contains cells or living organisms.

15. The structure as recited in claim 1 wherein said layer of low shear modulus material is bounded by a solid backing or support.

16. The structure as recited in claim 1 wherein both surfaces are coated with a layer of a gel.

17. The structure as recited in claim 1 wherein the electrical means for producing waves is electrostrictive.

18. The structure as recited in claim 1 wherein the electrical means for producing waves is thermoelastic.

19. The structure as recited in claim 1, including Lamb-wave reflecting means to form a Lamb-wave resonator.

20. An ultrasonic sensor comprising:
a composite structure comprising (a) a supporting frame of a first material, and (b) a propagation medium comprising a thin planar sheet of a second different material capable of supporting Lamb waves, supported peripherally by said supporting frame, said sheet having a thickness very much thinner than the wavelength of Lamb waves to be propagated thereon and having some physical characteristics determined by the value of a measurand acting thereon, said physical characteristics determining the propagation characteristics of Lamb waves to be propagated along the medium, said propagation medium including on a surface thereof a layer of a gel;
electrical means coupled to the thin planar sheet of said propagation medium for producing Lamb waves in the propagation medium;
output means on said sheet for producing an electrical signal representative of the determined propagation characteristics of the Lamb waves propagating along the propagation medium; and
measuring means for measuring selected characteristics of said electrical signal,
whereby when said sensor is acted on by a measurand, the physical characteristics of said propagation medium are determined and said electrical signal characteristics are also determined, so that said measuring means indicates the value of the measurand.

21. The sensor as recited in claim 20, wherein there is a ground plane that is substantially coextensive with the propagation medium.

22. The sensor as recited in claim 20, wherein at least a portion of the propagation medium is porous.

23. The sensor as recited in claim 22, wherein the porous portion of the propagation medium is also permeable.

24. The sensor as recited in claim 20, wherein a layer of sorptive material is disposed between said propagation medium and said gel layer.

25. The sensor as recited in claim 20, wherein a sorptive material is dispersed throughout said gel layer.

26. The sensor as recited in claim 20 further including a layer of protective material as an outer surface on said gel layer.

27. The sensor as recited in claim 26, wherein said protective layer is a material selected from the group consisting of Teflon and silicone.

28. The sensor as recited in claim 20, wherein said gel layer is a material selected from the group consisting of agar, gelatin, polyacrylamide, polyvinylalcohol, alginate, and other gels formed from seaweed, siloxanes, polyvinyl chloride gels, pectin, and the glycoprotein-based gel, mucus.

29. The sensor as recited in claim 20, wherein the propagation medium includes a means of heating said gel layer.

30. The sensor as recited in claim 20, wherein said gel layer contains cells or living organisms.

31. The sensor as recited in claim 20, wherein said gel layer is bounded by a solid backing or support.

32. The sensor as recited in claim 20, wherein both surfaces of the propagation medium are coated with a layer of a gel.

33. The sensor as recited in claim 20 wherein the electrical means for producing waves is electrostrictive.

34. The sensor as recited in claim 20 wherein the electrical means for producing waves is thermoelastic.

35. The sensor as recited in claim 20, wherein the electrical means includes means for producing both symmetrical and antisymmetrical Lamb waves in the propagation medium.

36. The sensor as recited in claim 35, wherein the propagation medium includes a layer of silicon nitride.

37. The sensor as recited in claim 36, wherein the propagation medium includes a layer of piezoelectric material.

38. The sensor as recited in claim 38, wherein the output means includes a receiving transducer, coupled to the propagation medium, for producing an electrical signal representative of the Lamb waves propagating along said propagation medium,
the electrical means includes a launching transducer, coupled to the propagation medium, for generating Lamb waves in the propagation medium,
a feedback path between the receiving and launching transducers for providing feedback from the receiving transducer to the launching transducer, and
a feedback amplifier in the feedback path for amplifying said electrical signal produced by the receiving transducer and fed back to the launching transducer, the sensor forming an oscillator in which Lamb waves are continuously propagated along the propagation medium,
the measuring means includes frequency measuring means for measuring the oscillation frequency.

39. The sensor as recited in claim 38, including Lamb wave reflecting means for reflecting Lamb waves generated by the launching transducer that propagate in directions away from the receiving transducer, so that the reflected Lamb waves do not produce an output at the receiving transducer.

40. The sensor as recited in claim 38, wherein each transducer includes a pair of interdigital finger electrodes formed on one surface of the layer of piezoelectric material.

41. The sensor as recited in claim 40, wherein the propagation medium includes a ground plane comprising a layer of conducting material on the surface of the piezoelectric layer opposite the surface on which the transducer electrodes are deposited, said ground plane being restricted to areas substantially opposite the transducer electrodes.

42. An ultrasonic structure comprising:
a propagation medium comprising a thin planar sheet capable of supporting Lamb waves, said sheet having a thickness very much thinner than the wavelength of the Lamb waves to be propagated thereon, said propagation medium including on a surface thereof a layer of a low shear modulus material; and
optical means for the thermoelastic generation of Lamb waves in the propagation medium.

* * * * *

UNITED STATES PATENT AND TRADEMARK OFFICE
CERTIFICATE OF CORRECTION

PATENT NO. : 5,212,988
DATED : May 25, 1993
INVENTOR(S) : Richard M. White et al.

It is certified that error appears in the above-indentified patent and that said Letters Patent is hereby corrected as shown below:

On title page, item [73] should read as follows:
—Assignee: The Regents of the University of California, Berkeley, Calif.—

Signed and Sealed this

Fourth Day of April, 1995

*Attest:*

BRUCE LEHMAN

*Attesting Officer*     *Commissioner of Patents and Trademarks*